United States Patent [19]

Tou et al.

[11] Patent Number: 4,677,220
[45] Date of Patent: Jun. 30, 1987

[54] PROCESS FOR THE PREPARATION OF α-L-ASPARTYL-L-PHENYLALANINE METHYL ESTER

[75] Inventors: Jacob S. Tou, Ballwin; Billy D. Vineyard, St. Louis, both of Mo.

[73] Assignee: Monsanto Company, St. Louis, Mo.

[21] Appl. No.: 793,601

[22] Filed: Oct. 31, 1985

[51] Int. Cl.$^4$ .................. C07C 102/00; C07C 103/52
[52] U.S. Cl. ........................................ 560/40; 560/41; 562/445; 426/548; 530/801
[58] Field of Search .................. 260/998.21; 546/247; 426/548; 562/571, 445; 548/478; 549/477, 253; 560/38, 40, 41; 530/801

[56] References Cited

U.S. PATENT DOCUMENTS

| 3,798,206 | 3/1974 | Uchiyama et al. | 260/998.21 |
| 3,798,207 | 3/1974 | Ariyoshi et al. | 260/998.21 |
| 3,879,372 | 4/1975 | Boesten | 260/998.21 |
| 3,920,626 | 11/1975 | Ariyoshi et al. | 426/217 |
| 3,962,207 | 6/1976 | Uchiyama et al. | 260/998.21 |
| 4,029,701 | 6/1977 | Haas et al. | 426/548 |
| 4,173,562 | 11/1979 | Bachman et al. | 260/998.21 |

FOREIGN PATENT DOCUMENTS 0127977 12/1984 European Pat. Off.
2140805A 12/1984 United Kingdom.

Primary Examiner—Morton Foelak
Assistant Examiner—Nathan M. Nutter
Attorney, Agent, or Firm—Dennis R. Hoerner, Jr.; James D. McNeil; James W. Williams, Jr.

[57] ABSTRACT

A regioselective process for the preparation of α-L-aspartyl-L-phenylalanine methyl ester is disclosed. A controlled aqueous coupling reaction between β-methyl-L-aspartate-N-carboxyanhydride and L-phenylalanine produces the aspartyl methyl ester of α-L-aspartyl-L-phenylalanine which is subsequently hydrolyzed and selectively esterified without isolation. The hydrochloride salt of α-L-aspartyl-L-phenylalanine methyl ester, which is selectively precipitated from the esterification mixture, can be neutralized to α-L-aspartyl-L-phenylalanine methyl ester.

22 Claims, No Drawings

PROCESS FOR THE PREPARATION OF α-L-ASPARTYL-L-PHENYLALANINE METHYL ESTER

BACKGROUND OF THE INVENTION

The present invention relates to an improved process for the synthesis of α-L-aspartyl-L-phenylalanine methyl ester (α-APM).

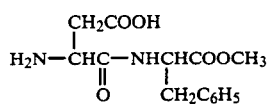

α-APM, first reported in 1969 by Mazur et al., *J. Amer. Chem. Soc.*, 91, 2684 (1969), is an artificial sweetener approximately two hundred times as sweet as sucrose. Since its discovery much effort has been directed toward an efficient synthesis.

Selective formation of a peptide bond in the α-position of the L-aspartic acid moiety poses a challenge to the synthesis of α-L-aspartyl-L-phenylalanine methyl ester. It has been shown that the ring opening reaction of N-substituted L-aspartic anhydride with L-phenylalanine or its methyl ester gives a mixture of α and β adducts, with a predominance of the α-isomer. Unfortunately, a separation/recovery step is necessary.

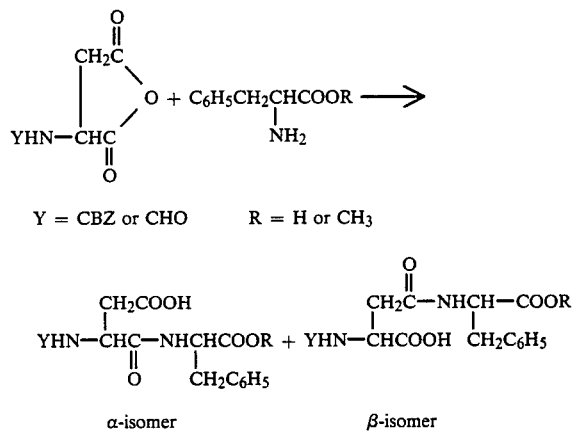

Alternately, several regioselective routes to the α-APM have also been reported by either enzymatic or chemical methods. For example, the approach by Vinick et al., *Tet. Letter.*, 1315 (1982), involves the coupling of L-phenylalanine methyl ester and L-aspartic acid N-thiocarboxyanhydride which was prepared from L-aspartic acid.

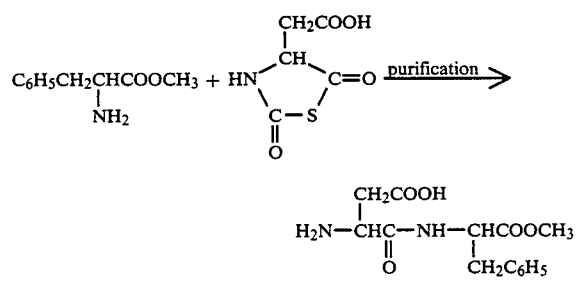

Unfortunately, regioselective routes to the α-dipeptide methyl ester reported heretofore are generally impractical. For example, preparation of α-APM from L-phenylalanine methyl ester and L-aspartic acid N-thiocarboxyanhydride as described above suffers from the disadvantage of using sulfur reactants which normally impart an unpleasant odor to the α-APM product. This odor is undesirable in view of the intended use of α-APM as a sweetening agent for foodstuffs and beverages.

Accordingly, the overall object of the present invention is to provide an improved regioselective route to α-APM.

DESCRIPTION OF THE INVENTION

The present invention provides an improved process for the synthesis of α-APM in which β-methyl-L-aspartate-N-carboxyanhydride (NCA) is reacted with L-phenylalanine to obtain α-L-aspartyl-L-phenylalanine-β-methyl ester which is then hydrolyzed and esterified without isolation. The hydrochloride salt of α-APM is selectively precipitated from the esterification media and can then be neutralized to its free amine to yield the desired product.

β-Methyl-L-aspartate hydrochloride, (β-methyl ester), a reactant in the preparation of NCA, is prepared from L-aspartic acid and anhydrous methanolic hydrogen chloride. Although the reaction of N-substituted aspartic anhydride with nucleophiles yields a predominantly α-isomeric product, the reverse is true when aspartic acid is esterified with excess hydrochloric acid. A β/α isomeric ratio of about 8:1 is obtained by esterification of aspartic acid in methanol.

The amount of excess hydrochloric acid employed in the above esterification reaction is important. While β-methyl-L-aspartate is the kinetically favored product, the thermodynamically favored diester product is formed if the reaction is conducted with longer reaction times and/or in the presence of greater amounts of excess hydrochloric acid.

Accordingly, reaction times between about 5 and about 10 hours and excess stoichiometric amounts of hydrochloric acid up to about 20 percent are preferred. It has been found that an optimal yield of β-methyl ester can be obtained in 6–8 hours with 10–15% excess hydrochloric acid.

After removal of most of the methanol, substantially pure β-methyl ester hydrochloride can be selectively precipitated by addition of a precipitating solvent, preferably isopropyl acetate, followed by cooling. Isopropyl acetate forms an azeotrope with methanol (80:20 v/v, methanol/acetate) that permits minimal loss of acetate upon recovery of solvent. Furthermore, β-methyl-L-aspartate hydrochloride is essentially insoluble in isopropyl acetate.

β-Methyl-L-aspartate-N-carboxyanhydride (NCA) is prepared by the reaction of β-methyl-L-aspartate hydrochloride with phosgene in tetrahydrofuran (THF) solution or any other non-interfering organic solvent.

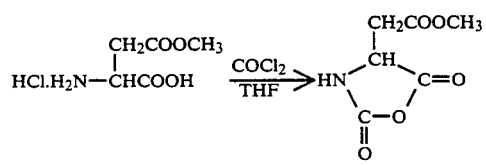

The reaction is conducted at a temperature between about 25° C. and about 65° C., and preferably about 60° C. Those skilled in the art will recognize that the specific temperature limit will necessarily depend on the boiling point of the particular solvent utilized. Typically, the reaction is carried out with an excess stoichiometric amount of phosgene, preferably below about 500 percent.

Unlike the starting material, NCA is very soluble in THF. Therefore, formation of a clear solution indicates completion of reaction. Excess phosgene is removed by rapidly passing a stream of nitrogen through the solution. THF can be removed by stripping the solvent under vacuum at a temperature below about 50° C., preferably about 35° C.

Solid NCA is obtained by precipitation at reduced temperature. The concentrated residue is contacted with an effective solvent system such as ethyl acetate and petroleum ether and cooling the resulting mixture. The vol/vol ratio of ethyl acetate and petroleum ether utilized in the crystallization procedure is preferably between about 0.2 and about 0.5 and most preferably about 0.4 NCA yield is typically between about 80–88 mole%. NCA can also be crystallized from a THF/heptane solution, in approximately the same proportions as stated above for ethyl acetate/petroleum ether system, with comparable NCA yields. Crystallization is preferably conducted at a temperature between about 0° C. and about 25° C. and preferably between about 0° C. and about 5° C. Alternately, non-isolated crude NCA can be utilized in the present process.

The regioselective reaction of L-phenylalanine and NCA to produce α-L-aspartyl-L-phenylalanine-β-methyl ester (aspartyl ester) is conducted in an aqueous medium with pH controlled preferably between about 9.5 and 11.0 and most preferably between about 10.0 and 10.5 by addition of suitable base.

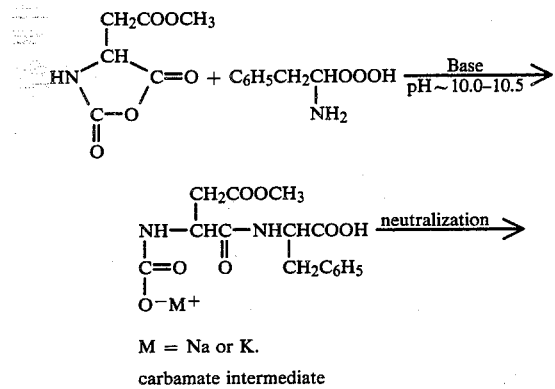

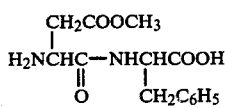

M = Na or K.

carbamate intermediate

The L-phenylalanine and NCA are reacted in proportions such that NCA is present in a slightly excess stoichiometric amount preferably below about 10% and most preferably about 5% or less. Suitable base for use in controlling the pH of the reaction mixture can be selected from the group consisting of sodium hydroxide, potassium hydroxide, sodium carbonate, potassium carbonate, sodium bicarbonate, potassium bicarbonate and mixtures thereof.

Typically, NCA is added as a solid to the amino acid solution. Alternately, NCA may be added as a solution in the selected solvent preferably THF. NCA concentrations in THF should range between about 2:1 and 1:2 and most preferably about 1:1 w/v.

There are three important process parameters which affect the efficiency of the coupling reaction. The stability of dipeptidyl carbamate, the chemical intermediate in the coupling reaction, is favored by relatively high pH. However, if the pH exceeds about 10.5, the hydrolysis of NCA and the formation of NCA anion will be increased because of the increased hydroxyl ion concentration. The result of that is the undesired aminolysis of the NCA and polymerization. The carbamate intermediate is stable in water at a temperature of about 0° C., but tends to lose carbon dioxide at room temperature. The low temperature control also minimizes the undesired carbamate exchange between the dipeptidyl carbamate and the incoming amino acid. As a result of carbamate exchange, a higher peptide will be formed (overreaction) and the L-phenylalanine starting material will be inactivated. Effective material mixing is known to be crucial for the controlled peptide synthesis. Rapid mixing provides a greater rate of dissolution of NCA and will suppress the carbamate exchange. It is also believed that rapid mixing minimizes the local depletion of L-phenylalanine and a high hydroxyl concentration which leads to the abovementioned aminolysis and polymerization reactions. Hence, the α-L-aspartyl-L-phenylalanine-β-methyl ester is obtained by addition of a sufficient amount of hydrochloric acid to neutralize the base added to promote the coupling, followed by warming the reaction mixture to permit release of carbon dioxide. Warming the reaction mixture to a temperature between about 10° C. and about 50° C. will be effective to promote product formation. Warming the mixture to a temperature of about 25° C. is preferred.

Depending on the purity of the reactant materials and the degree of conversion to desired product accomplished in the coupling reaction, contaminating organic by-products may be present. It is preferred that such by-products be removed at this stage in the process. Subsequent esterification reactions appear to proceed in a more efficient manner following by-product removal. It has been found that such materials can be removed by extraction with ethyl acetate or other immiscible extraction solvents capable of dissolving the organic by-products.

As a practical matter, the reaction mixture from the coupling reaction, or optionally following extraction, needs to be concentrated in order that the downstream hydrolysis/esterification reactions proceed in a more efficient manner. The large amount of inorganic salt formed as a result of neutralization of base in the coupling reaction, causes severe problems. Concentration of the reaction mixture resulted in massive precipitation of aspartyl ester and inorganic salt. Furthermore, the presence of high concentration of inorganic salt also affected the precipitation efficiency of α-L-aspartyl-L-phenylalanine methyl ester hydrochloride (α-APM.HCl) in the esterification step and lowered product purity since inorganic salt co-precipitated with α-APM.HCl.

While the obvious solution to the problems posed by the presence of salt is removal of interfering salt, attempts to remove salt and/or isolate pure aspartyl ester from the coupling mixture proved undesirable either because of poor crystallinity and/or low yields upon selected extraction. It has since been discovered that these problems can be obviated with additional advantageous results by conducting the process in the manner described below.

It was found that precipitation of aspartyl ester during the concentration stage in preparation for hydrolysis can be obviated by converting the aspartyl ester to the corresponding hydrochloride salt prior to concentration. Conversion to aspartyl ester hydrochloride is accomplished by addition of at least one equivalent of hydrochloric acid per equivalent of aspartyl ester to the reaction mixture of the coupling reaction. Hence in one aspect, the present invention provides a means of efficiently converting α-L-aspartyl-L-phenylalanine-β-methyl ester to α-L-aspartyl-L-phenylalanine in the presence of either sodium chloride and/or potassium chloride which comprises first converting the aspartyl ester to its hydrochloride salt.

Concentration can be effected in any conventional manner suitable for removal of the water or other solvent employed. Solvent is preferably removed by vacuum distillation until the aspartyl ester hydrochloride is preferably between about 30 wt% and about 60 wt% of the resulting mixture and more preferably between about 40 wt% and about 50 wt% of the mixture.

The aspartyl ester hydrochloride is hydrolyzed to selectively remove the methyl ester with minimal peptide bond cleavage by addition of hydrochloric acid and heating the mixture to obtain the α-L-aspartyl-L-phenylalanine hydrochloride (α-AP.HCl). To hydrolyze the aspartyl ester hydrochloride, acid is added such that the hydrochloric acid/aspartyl ester hydrochloride molar ratio is preferably between about 0.1 and about 4.5, more preferably between about 1.0 and about 3.0 and most preferably about 2.0.

The reaction is then heated to a temperature between about 25° C. and about 70° C. for a time between 24 hrs and 2 hrs. A higher reaction temperature will require shorter time for substantially complete reaction. A temperature between about 30° C. and about 50° C. is preferred. A reaction temperature of about 40° C. and reaction time of about 6 hours are most preferred when using the acid/aspartyl ester hydrochloride molar ratio of 2.0.

It was unexpectedly found that the sodium chloride and/or potassium chloride (inorganic salt) formed in the coupling reaction can be selectively precipitated from solution following conversion of the aspartyl ester hydrochloride to α-L-asparty-L-phenylalanine hydrochloride. The removal of such salt was found to be very selective since in the strongly acidic and highly concentrated mixture the dipeptide and other organic materials are very soluble while the inorganic salt is relatively insoluble and, therefore, can be separated. For example, in cases where sodium chloride is the salt formed, approximately 85% can be removed by this procedure. Hence, in another aspect, the present invention provides a means of easily removing sodium chloride and/or potassium chloride by selective precipitation in the presence of the hydrochloride salt of α-L-aspartyl-L-phenylalanine.

The degree of precipitation of dissolved sodium chloride and/or potassium chloride following formation of α-L-aspartyl-L-phenylalanine hydrochloride will depend upon the hydrolysis conditions. The particular concentration of α-L-aspartyl-L-phenylalanine-β-methyl ester hydrochloride, acid strength and reaction temperature should be selected such that a substantial portion of the inorganic salt precipitates. By "substantial" is meant that amount which results in minimal co-precipitation of inorganic salt with the α-L-aspartyl-L-phenylalanine methyl ester hydrochloride product from the esterification step described below. Those skilled in the art will recognize that the only limitation on the abovedescribed hydrolysis conditions are that the chosen conditions will result in selective precipitation of a substantial portion of inorganic salt during hydrolysis of the β-methyl ester substituent while not promoting peptide bond cleavage.

As disclosed in U.S. Pat. No. 4,173,562, issued Nov. 6, 1979 to Bachman et al., the α-L-aspartyl-L-phenylalanine hydrochloride can be selectively esterified to α-L-aspartyl-L-phenylalanine methyl ester hydrochloride. While such an esterification reaction results in the complex equilibrium shown below, the reaction is pushed to selective completion due to the relative insolubility of α-L-aspartyl-L-phenylalanine methyl ester hydrochloride.

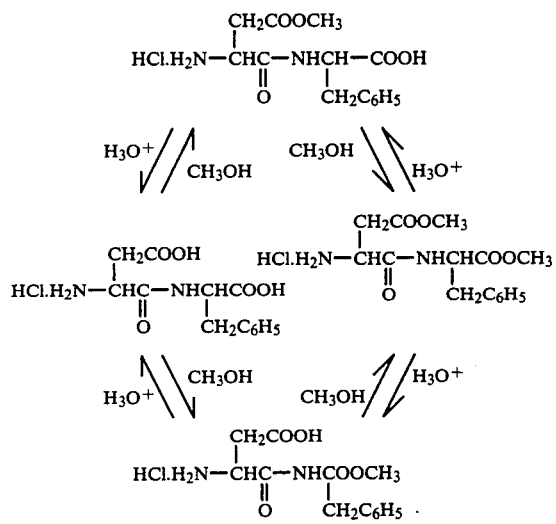

The esterification reaction is conducted by addition of methanol and hydrogen halide, preferably hydrochloric acid. Those skilled in the art will recognize that the reaction medium must also contain at least about 1.0 mole of methanol per mole of α-L-aspartyl-L-phenylalanine hydrochloride to ensure potentially complete reaction and higher levels of methanol can also be utilized. The additional hydrochloric acid which is added in this step, if needed, should be sufficient to ensure complete esterification and to promote precipitation of α-APM.HCl. A preferred amount is less than about 2.5 moles and most preferably about 0.5 moles of hydrochloric acid per mole of α-L-aspartyl-L-phenylalanine equivalent.

The temperatures utilized could be up to about the boiling point of the reaction mass, although the temperature utilized should be selected to minimize peptide bond cleavage. A range of from about 5° C. to about 50° C. is preferred and more particularly from about 20° C. to about 40° C. Although the most preferred temperature is near ambient temperature, it should be noted that higher temperatures tend to increase the rate of formation of α-APM but have the disadvantages of causing decomposition reactions and increasing the solubility of the hydrochloride salt of α-APM. On the other hand lower temperatures tend to decrease the rate of formation of α-APM.HCl, inhibit decomposition reactions and give higher levels of solid α-APM hydrochloride.

The solid hydrochloride salt of α-APM can be removed by solid/liquid separation procedures. Essentially, all the other compounds remain in the mother liquor and can be hydrolyzed, recovered and/or recycled. The solid hydrochloride salt of α-APM can then be converted to substantially pure α-APM by neutralization. An exemplary conversion process is disclosed in U.S. Pat. No. 4,173,562, supra.

The following examples are provided to better elucidate the above-description and practice of the present invention. It is to be understood that the specific details given in the examples are not to be construed as limiting, in any way, the scope of the invention.

Liquid chromatography was employed to follow the coupling, hydrolysis and esterification reactions and also for the quantitative analysis of aspartyl ester, α-AP.HCl and α-APM.HCl. A Water Associates LC system was used, including U6K injector, 6000A solvent delivery system, 450 variable wavelength detector ($\lambda=210$ nm) and a RCM-10 compressor with a $C_{18}$ or $C_8$ column. Eluting solvent was 20–35% acetonitrile/pH 3 buffer ($H_3PO_4$) solution. Unless otherwise noted, all percent yields are in mole percent.

EXAMPLES 1–6

β-Methyl-L-Aspartate Hydrochloride (β-Methyl Ester)

To methanol (500 ml) at 25°, gaseous HCl (0.89 mole) was bubbled into the solution over about 0.5 hr. L-Aspartic acid (0.77 mole) was added rapidly, then the resulting solution was held at 25° C. for 6.5 hrs. The methanol was stripped with an aspirator maintaining the pot temperature below 35° C. The batch became fairly thick when 145 ml (115 g) of methanol remained. Isopropyl acetate (435 ml) was added in about 0.5 hr, then the slurry was cooled to 0°–5° C. and held for 0.5 hr. Solid β-methyl-L-aspartate hydrochloride was collected and washed with 100 ml of isopropyl acetate. Dry wt.=100.2 g (70.6%) m.p. 192°–4°.

| Example No. | Time, Hrs.[a,b] | β/α[c] | $CH_3/CH_2$[d] | Yields, % | M.P. °C. |
|---|---|---|---|---|---|
| 2 | 7.5 | 7 | 1.45 | 76.2 | 193–5 |
| 3 | 7 | 8 | 1.48 | 71.8 | 193–5 |
| 4 | 8 | 8 | 1.5 | 71.8 | 193–5 |
| 5 | 7.5 | 8 | 1.47 | 67.5 | 194–6 |
| 6 | 7 | 8 | 1.4 | 68.4 | 194–6 |

[a]Esterification run at 25°.
[b]Batch stripped to approximately 50% concentration, then diluted with isopropyl acetate (isopropyl acetate/methanol ~3)
[c]Ratio of NMR peaks at δ 3.63 ppm and 3.7 ppm.
[d]Ratio of NMR methyl ester peaks and methylene peaks. Theoretical ratio for monoester is 1.5 and for the diester is 3.

EXAMPLES 7–14

β-Methyl-L-Asparate-N-Carboxyanhydride, (NCA)

Gaseous phosgene (95 g, 0.96 mole) was bubbled into a slurry of β-methyl-L-aspartate.HCl (80 g, 0.437 mole) in 800 ml THF. This mixture was then heated at 60° C. for 2 hrs. Batch became clear in 20 min. A rapid stream of $N_2$ was passed through the solution for one hour to remove excess phosgene. Solvent was stripped with an aspirator maintaining the pot temperature below 35° C. About 40 ml of ethyl acetate was added to the colorless residue followed by 30 ml of petroleum ether. Solid crystals of pure NCA were added and the cloudy solution was cooled to about 0° C. More petroleum ether (60 ml) was added to facilitate stirring after the occurrence of precipitation. Said NCA was collected after cooling overnight in a refrigerator. The white crystalline product weighted 64 g (84%) and had a melting point of 59°–61° C.

Elemental Analysis: cal: C=41.63, H=4.08, N=8.09. obs: C=41.71, H=3.97, N=7.82.

| Example No. | Reactants β-methylaspartate.HCl, gm | Phosgene gm | Crystallization EtOAc/ P.Ether (ml) | NCA yield, gm (%) |
|---|---|---|---|---|
| 8 | 17.8 | 11 | 30/100 | 15(86) |
| 9 | 27.5 | 25 | 40/160 | 22(86) |
| 10 | 25.4 | 23 | 10/50 | 23(95) |
| 11 | 15 | 20 | 15/30 | 11(80) |
| 12 | 48 | 70 | 30/65 | 37(81) |
| 13 | 40 | 52 | 20/70 | 31(83) |
| 14 | 80 | 106 | 40/160 | 65(86) |

EXAMPLES 15–18

α-L-Aspartyl-L-Phenylalanine-β-Methyl Ester (Aspartyl Ester)

L-Phenylalanine (15 g, 0.091 mole) was stirred in 200 ml of water at 0°–2° C. The pH of this solution was adjusted to 10.2 with 50% NaOH (~5 g). To this slurry, a solution of pure NCA (16.7 g, 0.091 mole) in 20 ml of THF was added in 15 min. with vigorous stirring. The pH was maintained at 10.0–10.2 by the addition of 7N NaOH solution. The resulting solution was then stirred at 0°–2° C. for 2 hrs. at the above pH range. Stoichiometric hydrochloric acid (18.8 g, 0.19 mole) was added to neutralize the sodium hydroxide and the solution warmed to 25° C. This clear solution (pH 4.15) was freeze-dried to give 38.8 g of solid (including 11 g of NaCl). LC quantitative analysis indicated a 78% yield of aspartyl ester based on L-phenylalanine.

In another run, L-Phe (28.9 gm,) was coupled with NCA (34 gm,) in a similar manner. The reaction mixture was neutralized with one equivalent of sulfuric acid. The freeze-dried material (81.7 g, containing 47 g of aspartyl ester as indicated by LC) was extracted twice with 600 ml of methanol (MeOH). The insoluble $Na_2SO_4$ (26.2 g) was removed by filtration and the filtrate was concentrated to about 300 ml. This slurry was cooled in the refrigerator overnight before filtering. The isolated yield of this salt-free aspartyl ester was 33.4 g (65%).

| Example No. | L-Phe, g. | NCA mole % Excess | Salt Formed | Aspartyl Ester, LC Yield, % |
|---|---|---|---|---|
| 17 | 3.6 | 4.7 | NaCl | 75 |
| 18 | 20.5 | 6.0 | NaCl | 84 |

Note:
1. Coupling reactions were conducted at 0–3° C. with pH maintained between 10.0~10.5.
2. Crystalline NCA was dissolved in 1:1 w/v of THF before addition.

EXAMPLES 19–21

α-L-Aspartyl-L-Phenylalanine Methyl Ester Hydrochloride (α-APM.HCl)

L-Phenylalanine (7.4 g, 0.045 mole) was stirred in 90 ml of water. The pH of this solution was adjusted to 10.2 (0°–2° C.) with 50% NaOH. Then a solution of pure NCA (8.3 g, 0.048 mole) in 8 ml of THF was added in 15 min. with vigorous stirring. The pH was maintained at 10.0–10.2 by the addition of 7N NaOH solution. The reaction mixture was then stirred at 0°–2° C. for 2 hr (pH 10.0–10.2). Sufficient 37% hydrochloric acid (9.7 g) was added at the end of the hold period to neutralize the NaOH. The solution was then warmed to 25° C. Liquid chromatography indicated an 80–82% yield of aspartyl ester based on L-phenylalanine. This clear solution was extracted twice with 50 ml portions of ethyl acetate. To the aqueous solution, 4.2 g of 37% HCl (0.043 mole) was added. The solution was concentrated under vacuum to a total weight of 31.1 g. Another 8.4 g (0.085 mole) of 37% HCl was added and the reaction slurry was held at 40° C. for 6 h to convert the aspartyl ester to α-L-aspartyl-L-phenylalanine hydrochloride. Solid (NaCl) was collected at 40° C. and washed with 2.6 g (0.026 mole) of 37% HCl and 7.5 g of methanol. Seed crystals were added to the combined filtrate and washings. The resulting solution was stirred at ambient temperature for 68 hours. The thick slurry was cooled to 0°–2° C. and the solid was collected by filtration and washed with 7 ml of cold water. The dry weight of α-APM.HCl was 9 g (55% yield based on L-phenylalanine). Product identity was confirmed by LC analysis.

| Example[a] No. | Hydrolysis[b,c] (moles per 100 gm medium) | | Esterification[d] (moles per 100 gm medium) | | | Yield[e] αAPM.HCl, % |
|---|---|---|---|---|---|---|
| | Aspartyl ester | HCl | Aspartyl ester | HCl | MeOH | |
| 20 | 0.10 | 0.25 | 0.08 | 0.28 | 0.61 | 41 |
| 21 | 0.12 | 0.29 | 0.10 | 0.32 | 0.70 | 50 |

[a]The NCA coupling parameters are the same as in Example 19.
[b]Hydrolysis was carried out at 60° C. for 2 hrs.
[c]Approximately 57% and 82% of the theoretical amount of NaCl were removed in Examples 20 and 21, respectively.
[d]Esterification reactions were run at room temperature for 69 hrs.
[e]Yields were based on L-Phe.

EXAMPLE 22

α-L-Aspartyl-L-Phenylalanine Methyl Ester (α-APM)

A slurry of α-APM.HCl (9 g) and water (51 g) was stirred, heated and maintained at 45° C. until the solid dissolved. The pH was adjusted to 2.9 with sodium hydroxide (8.3 g of 4.8 wt% NaOH). The batch was seeded with crystals of α-APM and stirred for about 1 hour at 40°–43° C. The pH of the batch was adjusted to 4.2 with additional sodium hydroxide (12.6 g of 4.8 wt% of NaOH) over 1.5 hours and maintained at 40°–43° C. for an additional 0.5 hour. The batch was then cooled and maintained at a temperature between 0° C. and 5° C. for 1 hour. The α-APM which precipitated was filtered from solution and washed with 42 ml of cold water. Approximately 5.9 grams of dry α-APM were recovered. The product exhibited a $[\alpha]_D^{20} = 30.3°$ (c 1.0, HOAc); authentic sample $[\alpha]_D^{20} = 30.1°$ (c 1.0, HOAc).

We claim:

1. A process for producing α-L-aspartyl-L-phenylalanine hydrochloride from α-L-aspartyl-L-phenylalanine-β-methyl ester in the presence of sodium chloride and/or potassium chloride which comprises:
   (a) contacting the α-L-aspartyl-L-phenylalanine-β-methyl ester with a sufficient amount of hydrochloric acid to produce α-L-aspartyl-L-phenylalanine-β-methyl ester hydrochloride;
   (b) hydrolyzing the α-L-aspartyl-L-phenylalanine-β-methyl ester hydrochloride in the presence of additional hydrochloric acid to remove the β-methyl ester substituent, said hydrolysis being conducted at an effective α-L-aspartyl-L-phenylalanine-β-methyl ester hydrochloride concentration, acid strength and temperature to cause selective precipitation of a substantial portion of the sodium chloride and/or potassium chloride from the reaction mixture.

2. The process of claim 2 in which the hydrolysis reaction is conducted at an α-L-aspartyl-L-phenylalanine-β-methyl ester hydrochloride concentration between about 30 wt% and about 60 wt%.

3. The process of claim 1 in which the hydrolysis reaction is conducted at a temperature between about 25° C. and about 70° C.

4. The process of claim 1 in which the hydrolysis reaction is conducted at an acid strength corresponding to a hydrochloric acid/α-L-aspartyl-L-phenylalanine-β-methyl ester hydrochloride molar ratio between about 0.1 and about 4.5.

5. The process of claim 1 in which the hydrolysis reaction is conducted at an α-L-aspartyl-L-phenylalanine-β-methyl ester hydrochloride concentration between 40 wt% and 50 wt%, an acid strength corresponding to an acid/methyl ester hydrochloride ratio of between 1.0 and about 3.0 and a temperature between about 30° C. and about 50° C.

6. A process for producing α-L-aspartyl-L-phenylalanine hydrochloride which comprises:
   (a) coupling L-phenylalanine with β-methyl-L-aspartate-N-carboxyanhydride in an aqueous solvent under alkaline conditions using a sodium and/or potassium base followed by neutralization of the base by addition of hydrochloric acid and decarboxylation of the N-carboxy-α-L-aspartyl-L-phenylalanine-β-methyl ester intermediate to produce α-L-aspartyl-L-phenylalanine-β-methyl ester and by-product sodium chloride and/or potassium chloride;
   (b) contacting the α-L-aspartyl-L-phenylalanine-β-methyl ester with a sufficient amount of hydrochloric acid to produce α-L-aspartyl-L-phenylalanine-β-methyl ester hydrochloride;
   (c) hydrolyzing the α-L-aspartyl-L-phenylalanine-β-methyl ester hydrochloride in the presence of additional acid to remove the β-methyl ester substituent, said hydrolysis conducted at an effective α-L-aspartyl-L-phenylalanine-β-methyl ester hydrochloride concentration, acid strength and temperature to cause selective precipitation of a substantial portion of the sodium chloride and/or potassium chloride from the reaction mixture.

7. The process of claim 6 in which the reaction mixture is extracted, following the coupling reaction, with an immiscible solvent to remove organic by-products.

8. The process of claim 6 in which the coupling reaction is conducted at a pH between about 9.5 and about 11.0.

9. The process of claim 6 in which the alkaline conditions of the coupling reaction are maintained by addition of a potassium or sodium base selected from the group consisting of sodium hydroxide, potassium hydroxide, sodium carbonate, potassium carbonate, sodium bicarbonate, potassium bicarbonate and mixtures thereof.

10. The process of claim 6 in which decarboxylation of the N-carboxy-α-L-aspartyl-L-phenylalanine-β-methyl ester intermediate of the coupling reaction is accomplished following neutralization of base by warming the reaction mixture to between 10° C. and 50° C.

11. The process of claim 6 in which the hydrolysis reaction is conducted at a α-L-aspartyl-L-phenylalanine-β-methyl ester hydrochloride concentration between about 30 wt% and 60 wt%.

12. The process of claim 6 in which the hydrolysis reaction is conducted at a temperature between about 25° C. and 70° C.

13. The process of claim 6 in which the hydrolysis reaction is conducted at an acid strength corresponding to an acid/α-L-aspartyl-L-phenylalanine-β-methyl ester hydrochloride molar ratio between about 0.1 and about 4.5.

14. The process of claim 7 in which the hydrolysis is conducted at an α-L-aspartyl-L-phenylalanine-β-methyl ester hydrochloride concentration between 40 wt% and 50 wt% an acid strength corresponding to an acid/methyl ester hydrochloride molar ratio of between about 1.0 and about 3.0 and a temperature between about 30° C. and about 50° C.

15. A process for producing α-L-aspartyl-L-phenylalanine methyl ester which comprises:
(a) coupling L-phenylalanine with β-methyl-L-aspartate-N-carboxyanhydride in an aqueous solvent under alkaline conditions, using a sodium and/or potassium base followed by neutralization of the base by addition of hydrochloric acid and decarboxylation of the N-carboxy-α-L-aspartyl-L-phenylalanine-β-methyl ester intermediate to produce α-L-aspartyl-L-phenylalanine-β-methyl ester and by-product sodium chloride and/or potassium chloride;
(b) contacting the α-L-aspartyl-L-phenylalanine-β-methyl ester with a sufficient amount of hydrochloric acid to produce α-L-aspartyl-L-phenylalanine-β-methyl ester hydrochloride;
(c) hydrolyzing the α-L-aspartyl-L-phenylalanine-β-methyl ester hydrochloride in the presence of additional hydrochloric acid to remove the β-methyl ester substituent, said hydrolysis conducted at an effective α-L-aspartyl-L-phenylalanine-β-methyl ester hydrochloride concentration, acid strength and temperature to cause selective precipitation of a substantial portion of the sodium chloride and/or potassium chloride from the reaction mixture;
(d) esterifying the α-L-aspartyl-L-phenylalanine hydrochloride in the presence of hydrochloric acid and methanol, said esterification being conducted at an α-L-aspartyl-L-phenylalanine hydrochloride concentration and acid strength to cause selective precipitation of α-L-aspartyl-L-phenylalanine methyl ester hydrochloride;
(e) neutralizing α-L-aspartyl-L-phenylalanine methyl ester hydrochloride to produce the α-L-aspartyl-L-phenylalanine methyl ester product.

16. The process of claim 15 in which the reaction mixture is extracted, following the coupling reaction, with an immiscible solvent to remove organic by-products.

17. The process of claim 15 in which the alkaline conditions of the coupling reaction are maintained by addition of a potassium or sodium base selected from the group consisting of sodium hydroxide, potassium hydroxide, sodium carbonate, potassium carbonate, sodium bicarbonate, potassium bicarbonate and mixtures thereof.

18. The process of claim 15 in which decarboxylation of the N-carboxy-α-L-aspartyl-L-phenylalanine-β-methyl ester intermediate of the coupling reaction is accomplished following neutralization of base by warming the reaction mixture to between 10° C. and 50° C.

19. The process of claim 15 in which the esterification reaction is conducted in the presence of at least about one mole of methanol per mole of α-L-aspartyl-L-phenylalanine hydrochloride.

20. The process of claim 15 in which the additional hydrochloric acid added during the esterification reaction is less than about 2.5 moles of hydrochloric acid per mole of α-L-aspartyl-L-phenylalanine hydrochloride.

21. The process of claim 15 in which the esterification reaction is conducted at a temperature between about 20° C. and about 40° C.

22. The process of claim 16 in which the hydrolysis is conducted at an α-L-aspartyl-L-phenylalanine-β-methyl ester hydrochloride concentration between 40 wt% and 50 wt%, an acid strength corresponding to an acid/methyl ester hydrochloride molar ratio between about 1.0 and about 3.0 and a temperature between about 30° C. and about 50° C.

* * * * *